United States Patent
Scheyer et al.

(10) Patent No.: US 7,132,433 B2
(45) Date of Patent: *Nov. 7, 2006

(54) USE OF (+)-α-(2,3-DIMETHOXYPHENYL)-1-[2-(4-FLUOROPHENYL)ETHYL]-4-PIPERIDINEMETHANOL OR ITS PRODRUG IN THE TREATMENT OF BEHAVIORAL OR PSYCHOLOGICAL SYMPTOMS ASSOCIATED WITH A DISEASE

(75) Inventors: Richard D. Scheyer, Branchburg Township, NJ (US); Stephen M. Sorensen, Chester, NJ (US); Janice M. Hitchcock, Fishers, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 8 days.

This patent is subject to a terminal disclaimer.

(21) Appl. No.: 10/838,035

(22) Filed: May 3, 2004

(65) Prior Publication Data
US 2004/0204457 A1  Oct. 14, 2004

Related U.S. Application Data

(63) Continuation of application No. 10/217,843, filed on Aug. 13, 2002, now abandoned, which is a continuation of application No. 09/861,980, filed on May 18, 2001, now abandoned.

(60) Provisional application No. 60/206,943, filed on May 25, 2000.

(51) Int. Cl.
A61K 31/445 (2006.01)
(52) U.S. Cl. .................................. 514/317
(58) Field of Classification Search ................ 514/317
See application file for complete search history.

(56) References Cited

U.S. PATENT DOCUMENTS

| | | | |
|---|---|---|---|
| 4,783,471 A | 11/1988 | Carr | |
| 4,877,798 A | 10/1989 | Sorensen | |
| 4,908,369 A | 3/1990 | Schlecter et al. | |
| 4,912,117 A | 3/1990 | Carr et al. | |
| 5,021,428 A | 6/1991 | Carr et al. | |
| 5,106,855 A | 4/1992 | McLees | |
| 5,134,149 A | 7/1992 | Carr et al. | |
| 5,169,096 A | 12/1992 | Carr et al. | |
| 5,561,144 A | 10/1996 | Carr et al. | |
| 5,618,824 A | 4/1997 | Schmidt et al. | |
| 5,700,812 A | 12/1997 | Carr et al. | |
| 5,700,813 A | 12/1997 | Carr et al. | |
| 5,721,249 A | 2/1998 | Carr et al. | |
| 6,004,980 A | 12/1999 | Carr et al. | |
| 6,028,083 A | 2/2000 | Carr et al. | |
| 6,063,793 A * | 5/2000 | Carr et al. ................ | 514/317 |
| 6,455,526 B1 * | 9/2002 | Kohn et al. ................ | 514/248 |

FOREIGN PATENT DOCUMENTS

| | | |
|---|---|---|
| EP | 0796619 | 9/1997 |
| WO | 99/20315 * | 4/1999 |
| WO | WO 00/12090 | 3/2000 |

OTHER PUBLICATIONS

Carlos H. Rojas-Fernandez et al., Dementia with Lewy Bodies: Review and Pharmacotherapeutic Implications, Pharmacotherapy (1999, pp. 795-803, vol. 19, No. 7).

Carlsson et al, J. Neural Transm., (1999, vol. 106, pp. 123-129).

Clive Ballard et al., Psychiatric Morbidity in Dementia With Lewy Bodies: A Prospective Clinical and Neuropathological Comparative Study with Alzheimer's Disease, Am J. Psychiatry (1999, pp. 1039-1045, vol. 156, No. 7).

I. G. McKeith et al., What are the relations between Lewy body disease and AD?, J. Neural Transm (1998, pp. 107-116, vol. 54).

John H. Kehne et al., Preclinical Characterization of the Potential of the Putative Atypical Antipsychotic MDL 100,907 as a Potent 5HT2a Antagonist with a Favorable CNS Safety Profile, Journal of Pharmacology and Experimental Therapeutic (1996, pp. 968-981, vol. 277).

* cited by examiner

*Primary Examiner*—Phyllis G. Spivack
(74) *Attorney, Agent, or Firm*—Balaram Gupta

(57) ABSTRACT

The present invention is directed to use of (+)-α-(2,3-dimethoxyphenyl)-1-[2-(4-fluorophenyl)ethyl]-4-piperidinemethanol or its prodrug depicted as Formula II, wherein R is $C_{1-20}$alkyl, in treating patients for behavioral or psychological symptoms associated with Alzheimer's disease, Lewy body dementia or Parkinson's disease.

Formula II

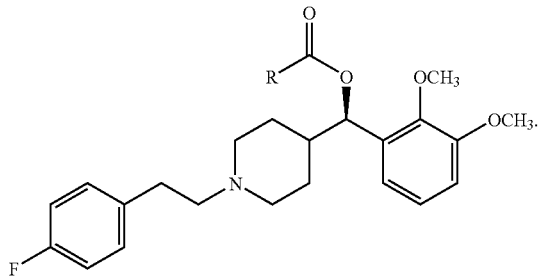

8 Claims, No Drawings

USE OF (+)-α-(2,3-DIMETHOXYPHENYL)-1-[2-(4-FLUOROPHENYL)ETHYL]-4-PIPERIDINEMETHANOL OR ITS PRODRUG IN THE TREATMENT OF BEHAVIORAL OR PSYCHOLOGICAL SYMPTOMS ASSOCIATED WITH A DISEASE

This application is a continuation of U.S. application Ser. No. 10/217,843, filed Aug. 13, 2002 now abandoned, which is a continuation of U.S. application Ser. No. 09/861,980, filed, May 18, 2001, now abandoned, which claims the benefit of U.S. Provisional Application No. 60/206,943, filed May 25, 2000.

Dementias are neurodegenerative diseases characterized by learning and cognitive deficiencies and are typically accompanied by behavioral symptoms, psychological symptoms and motor symptoms. Dementias include Alzheimer's disease, Lewy body dementia, vascular dementia, dementia in Parkinson's disease, fronto-temporal dementia, Pick's disease and corticobasal degeneration.

Alzheimer's disease, accounting for 50–60% of cases, is the most common form of dementia. The second most common form was believed to be vascular dementia. Dementia with Lewy bodies (DLB) is a recently identified form that may account for a substantial number of cases, and now is proposed to be the second most common type of dementia (*Pharmacotherapy* (1999) 19(7): 795–803 at 795; *J Neural Transm* (1998)[Suppl] 54:107–116 at 107). Lewy bodies are spherical inclusion bodies seen in the brain stem nuclei of patients with Parkinson's disease. Recently, they were identified in cerebral and limbic cortices as well. Lewy bodies predominantly contain neurofilaments and other proteins such as ubiquitin. The origin of their development is unknown.

Alzheimer's disease and DLB can be distinguished at the molecular level and through clinical observation. Alzheimer's disease is characterized by deposits of amyloid protein and hyperphosphorylation of the microtubular associated protein tau, and DLB by neurofilament abnormalities including phosphorylation, ubiquitination, proteolysis, and cross-linking of constituent proteins. The two diseases appear therefore to be distinct at an ultrastructural and molecular level, a conclusion which is consistent with the fact that the clinical syndromes associated with DLB and Alzheimer's disease are sufficiently differentiated to allow for accurate antemortem diagnosis (*J Neural Transm* (1998) [Suppl] 54:107–116 at 107).

The presence of psychopathology early in the disease course distinguishes DLB from other dementias (*Am J Psychiatry* 156(7): 1039–45). The Parkinsonian motor features are typically mild, spontaneous features such as bradykinesia and rigidity. Masked faces, hypophonia and a slow shuffling gait are also common. Patients treated with levodopa respond poorly and the drug can exacerbate or cause hallucinations (*Pharmacotherapy* 1999: 19(7) 795–803 at 796).

Patients with Parkinson's disease often develop dementia as the disease progresses, and hallucinations are a common side effect of levodopa therapy ("dopamine induced psychosis"). If the onsets of dementia and Parkinson's symptoms occur within 12 months of each other, a diagnosis of DLB can be made. The symptoms of myoclonus, absence of rest tremor, lack of response to levodopa, or no perceived need to administer levodopa are 10 times more likely in DLB than in Parkinson's disease Id. at 798. Since the compounds of the present invention have very little activity at the dopamine receptor (unlike some other $5HT_{2A}$ antagonists), these compounds are useful in treating patients susceptible to dopamine induced psychosis.

Increased sensitivity to neuroleptic agents is another important indicator in DLB and has significant pharmacotherapeutic implications. Many patients require neuroleptics to treat psychotic symptoms, but neuroleptics can exacerbate the parkinsonian symptoms (extrapyramidal symptoms, "EPS") in DLB. Therefore, neuroleptics in DLB must be prescribed with caution, if at all. Id. at 796. The compounds of the present invention do not exacerbate EPS.

The combination of the sensitivity to neuroleptic agents, the age and condition of the patient, and the symptoms manifested in DLB produce a quandary for the physician in prescribing medication. There have been many suggestions for therapy published, but all therapies have had limited or mixed success.

Pick's disease is a dementing disorder primarily involving the frontal and temporal lobes. It is characterized clinically by an insidious mid-life onset (50–65 years of age) of personality and behavioral changes, disinhibition, impairment of language function and decline in memory and intellect. NEUROPATHY OF DEMENTING DISORDERS, Wm. R. Markesberry, MD, editor, Arnold, Hodder Headline.

Fronto-Temperoral dementia is a dementing disorder characterized by degeneration of the frontal and anterior temporal lobe.

Corticobasal degeneration is a dementing disorder which is predominantly an extrapyramidal motor disorder.

It is an object of the present invention to treat symptoms of dementias. Such symptoms include:
  a) Behavioral symptoms such as sleep disturbances, delirium (including fluctuations), aggression and agitation;
  b) Psychological symptoms such as hallucinations, delusions, anxiety and depression;
  c) Motor symptoms which means impaired ability to carry out motor activities despite intact motor function; and
  d) Learning and cognitive impairment, for example, impaired ability to learn new information or to recall previously learned information (e.g., impaired social memory), aphasia, apraxia, agnosia, disturbance in executive functioning, etc.

It is also an object of the present invention to treat dopamine induced psychosis. Another object is to treat patients for dementia, or dopamine induced psychosis having Parkinson's disease or DLB, without exacerbating or creating EPS or dopamine induced psychosis.

A compound of the present invention, (+)-α-(2,3-dimethoxyphenyl)-1-[2-(4-fluorophenyl)ethyl]-4-piperidinemethanol, or its pharmaceutically acceptable salt, is a potent antagonist at the serotonin $5HT_{2A}$ receptor (*J. Pharm. Exp. Ther.* (1996) 277:968–9881) incorporated herein by reference. It was described in U.S. Pat. No. 5,134,149, incorporated herein by reference.

Other compounds of the present invention include prodrugs of (+)-α-(2,3-dimethoxyphenyl)-1-[2-(4-fluorophenyl)ethyl]-4-piperidinemethanol, or its pharmaceutically acceptable salt, which mean that a compound is administered which is different from (+)-α-(2,3-dimethoxyphenyl)-1-[2-(4-fluorophenyl)ethyl]-4-piperidinemethanol but (+)-α-(2,3-dimethoxyphenyl)-1-[2-(4-fluorophenyl)ethyl]-4-piperidinemethanol becomes available in the body after metabolism. As used herein, "prodrug" has the specific meaning of the compounds disclosed in U.S. Pat. No. 6,028,083, incorporated herein by reference, shown hereafter as Formula II:

FORMULA II

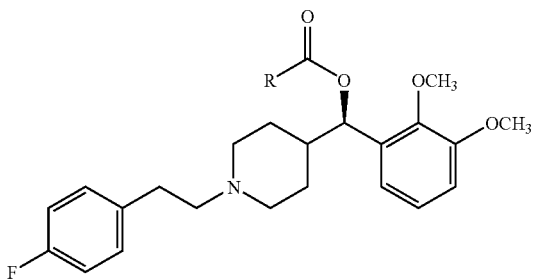

wherein R is $C_1$–$C_{20}$ alkyl, or a stereoisomer or a pharmaceutically acceptable salt thereof. "Alkyl" means a branched or straight chain alkyl group specified by the amount of carbons in the alkyl group, e.g., $C_1$–$C_{20}$ alkyl means one, two, three, four, five, six, seven, eight, nine, ten eleven, twelve, thirteen, fourteen, fifteen, sixteen, seventeen, eighteen, nineteen, or twenty carbon branched or straight chain alkyl or ranges thereof, for example, but not limited to $C_1$–$C_{15}$, $C_5$–$C_{20}$, $C_3$–$C_{15}$, $C_5$–$C_{15}$, $C_7$–$C_{15}$ and $C_7$ to $C_9$.

(+)-α-(2,3-Dimethoxyphenyl)-1-[2-(4-fluorophenyl)ethyl]-4-piperidinemethanol antagonizes the effects of serotonin at the $5HT_{2A}$ receptor and thus is useful for treating a variety of conditions. Some of the uses for (+)-α-(2,3-dimethoxyphenyl)-1-[2-(4-fluorophenyl)ethyl]-4-piperidinemethanol have been disclosed in patents and patent applications. U.S. Pat. No. 5,169,096 claimed compounds having a generic scope which encompassed the (+)-α-(2,3-dimethoxyphenyl)-1-[2-(4-fluorophenyl)ethyl]-4-piperidinemethanol and disclosed uses of the treatment of anorexia nervosa, variant angina, Raynaud's phenomenon, coronary vasospasms, prophylactic treatment of migraine, cardiovascular diseases such as hypertension, peripheral vascular disease, thrombotic episodes, cardiopulmonary emergencies and arrythmias, and has anesthetic properties. See also U.S. Pat. Nos. 4,783,471; 4,912,117; and 5,021,428, which are divisions of U.S. Pat. No. 5,169,096. See also U.S. Pat. No. 4,877,798 (fibromyalgia), U.S. Pat. No. 4,908,369 (insomnia); U.S. Pat. No. 5,106,855 (glaucoma); U.S. Pat. No. 6,004,980 (anxiety, Raynauds phenomenon, cardiac arrhythmia; extrapyramidal symptoms; drug abuse, anorexia, fibromylagia). All of the foregoing are incorporated herein by reference.

The (+)-α-(2,3-dimethoxyphenyl)-1-[2-(4-fluorophenyl)ethyl]-4-piperidinemethanol was then specifically claimed in U.S. Pat. No. 5,134,149 which disclosed uses of antagonizing serotonin at the 5HT2 receptor, treating anxiety, variant angina, anorexia nervosa, Raynaud's phenomenon, intermittent claudication, coronary or peripheral vasospasms, fibromyalgia, extrapyramidal symptoms, arrythmias, thrombotic illness, transient ischemic attacks, drug abuse, and psychotic illness such as schizophrenia and mania. See also U.S. Pat. Nos. 5,561,144; 5,700,812; 5,700,813; 5,721,249-divisionals of U.S. Pat. No. 5,134,149-and also U.S. Pat. Nos. 5,618,824 (obsessive compulsive disorder) and PCT/US97/02597 (depressive disorders including major depressive episode and dysthymia, and bipolar disorder), and insomnia and sleep apnea, incorporated herein by reference.

DETAILED DESCRIPTION OF THE INVENTION

Terms used herein have the meanings defined here and elsewhere in this specification.

a) "Pharmaceutically acceptable salts" means either an acid addition salt or a basic addition salt, whichever is possible to make with the compounds of the present invention.

"Pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

b) "Patient" means a warm blooded animal, such as for example rat, mice, dogs, cats, guinea pigs, and primates such as humans.

c) "Treat" or "treating" means to alleviate symptoms, eliminate the causation of the symptoms either on a temporary or permanent basis, or to prevent or slow the appearance of symptoms of the named disorder or condition.

d) "Therapeutically effective amount" means an amount of the compound which is effective in treating the named disorder or condition.

e) "Pharmaceutically acceptable carrier" is a non-toxic solvent, dispersant, excipient, adjuvant or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

f) "Sleep Disturbances" means fragmented sleep, narcolepsy and "REM" or "Rapid Eye Movement" behavior disorder, restless legs and/or periodic limb movements.

g) "EPS" or "Extrapyramidal symptoms" are symptoms which may manifest upon administration of neuroleptic drugs. The symptoms include a parkinsonian-like syndrome wherein the patient experiences muscular rigidity and tremors. Some experience akathesia and acute dystonic reactions.

h) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

i) M100907 means (+)-isomer of α-(2,3-dimethoxyphenyl)-1-[2-(4-fluorophenyl)ethyl]-4-piperidinemethanol.

The (+)-isomer of α-(2,3-dimethoxyphenyl)-1-[2-(4-fluorophenyl)ethyl]-4-piperidinemethanol can be prepared by methods described in U.S. Pat. No. 5,134,149. One suitable method follows.

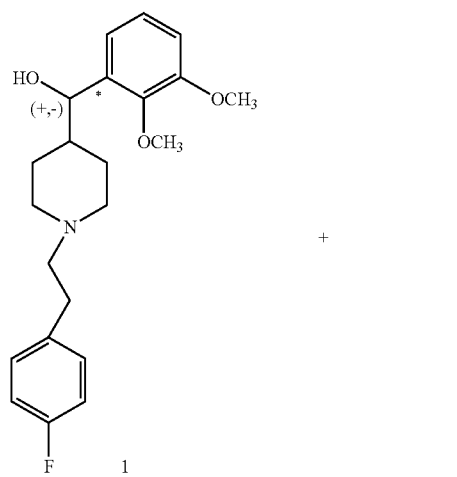

SCHEME I- Starting Materials

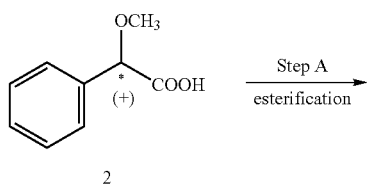

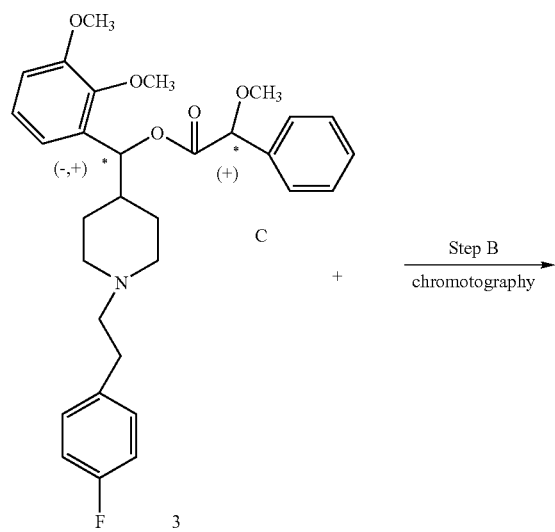

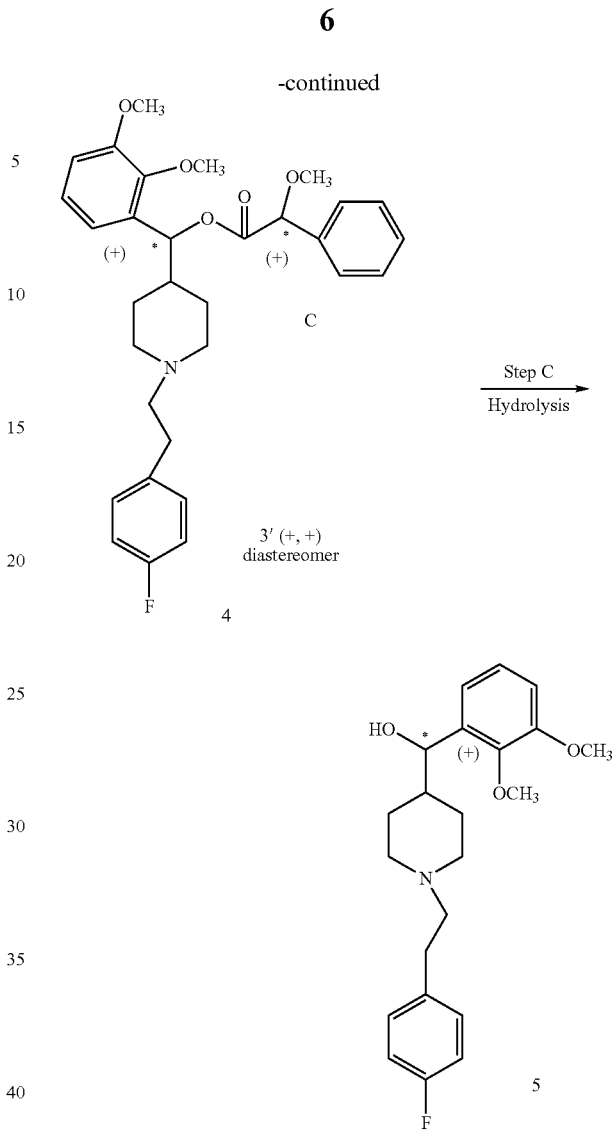

In Step A of Reaction Scheme I, an esterification reaction is carried out between racemic alpha-(2,3-dimethoxyphenyl)-1-[2-(4-fluorophenyl)ethyl]-4-piperidinemethanol (structure 1) and the (+)-isomer of alphamethoxyphenylacetic acid (structure 2). This esterification produces the diastereomeric mixture identified as structure 3. These diastereomers are subjected to silica gel chromatography which separates the two diastereomers, thereby isolating the (+,+) diastereomer as is depicted in Step B. In Step C, the (+,+) diastereomer is hydrolyzed which produces the (+)-isomer of alpha(2,3-dimethoxyphenyl)-1-[2-(4-fluorophenyl)ethyl]-4-piperidinemethanol.

The esterification reaction can be carried out using techniques known in the art. Typically approximately equivalent amounts of racemic alpha-(2,3-dimethoxyphenyl)-1-[2-(4-fluorophenyl)ethyl]-4-piperidinemethanol and the (+)-isomer of alpha-methoxyphenylacetic acid are contacted in an organic solvent such as methylene chloride, THF, chloroform, or toluene and heated to reflux for a period of time ranging from 5 to 24 hours. The esterification is typically carried out in the presence of an equivalent amount of dicyclohexylcarbodiimide (DCC) and a catalytic amount of 4-dimethylaminopyridine (DMAP). The resulting diastereomers can be isolated by filtration of the dicyclohexylurea and evaporation of the filtrate.

The diastereomers are then subjected to silica gel chromatography which separates the (+,+) and the (−,+) diastereomers. This chromatographic separation may be carried out as is known in the art. A 1:1 mixture of hexane and ethyl acetate is one suitable eluent.

The resulting (+,+) diastereomer is then subjected to a hydrolysis reaction which produces the (+)-enantiomer of alpha-(2,3-dimethoxyphenyl)-1-[2-(4-fluorophenyl)ethyl]-4-piperidinemethanol. The hydrolysis is carried out by contacting the diastereomer with an excess of a base such as potassium carbonate in an aqueous alcoholic solution. The hydrolysis is carried out at a temperature of about 15 to 30° C. for a period of time ranging from 2 to 24 hours. The resulting (+)-isomer of alpha-(2,3-dimethoxyphenyl)-1-[2-(4-fluorophenyl)ethyl]-4-piperidinemethanol may then be recovered by dilution with water and extraction with methylene chloride. It is then purified by recrystallization from a solvent system such as cyclohexane/hexane or ethyl acetate/hexane.

Methods for producing the starting materials of Reaction Scheme I are known in the art. For example, U.S. Pat. No. 4,783,471 teaches how to prepare racemic alpha-(2,3-dimethoxyphenyl)-1-[2-(4-fluorophenyl)ethyl]-4-piperidinemethanol. This patent is hereby incorporated by reference. Examples No. 1 and 2 of this application also teach suitable methods. Alternatively, racemic alpha-(2,3-dimethoxyphenyl)-1-[2-(4-fluorophenyl)ethyl]-4-piperidinemethanol can be prepared in the following manner. Initially 4-hydroxypiperidine is subjected to an N-alkylation reaction with p-fluorophenylethyl bromide which produces 4-hydroxy-1-[2-(4-fluorophenyl)ethyl]-piperidine. This compound is brominated with $Ph_3P \cdot Br_2$ which produces 4-bromo-1-[2-(4-fluorophenyl)ethyl]piperidine. This compound is contacted with Mg thereby forming a Grignard Reagent which is then reacted with 2,3-dimethoxybenzaldehyde which produces the desired product (±)-alpha-(2,3-dimethoxyphenyl)-1-[2-(4-fluorophenyl)ethyl]-4-piperidinemethanol. The (+)-isomer of alphamethoxyphenylacetic acid is known in the art.

Scheme II shows the synthesis of the compounds of Formula II, Prodrugs.

SCHEME II

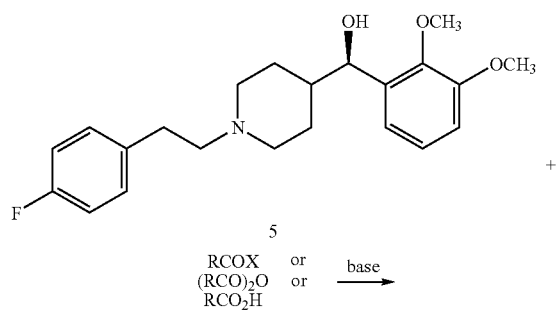

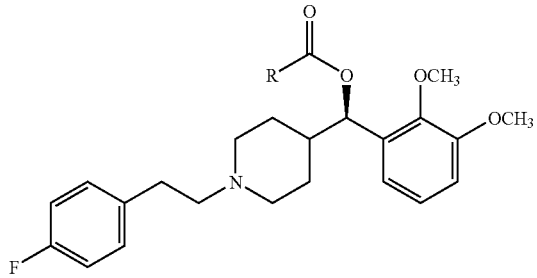

FORMULA II

Referring to Scheme II, X is chloro or bromo, with chloro being preferred and R is as previously defined. This reaction scheme shows the making of the sustained release compounds of Formula I from the alcohol (5).

The alcohol (5) is reacted with an acid halide (RC(O)X), $RCO_2H$ or acid anhydride $(RCO)_2O$ in the presence of an a sufficient amount of an appropriate base. An appropriate base is one that permits ester formation from the acid halide or anhydride. Examples of appropriate bases are trialkylamines, pyridine such as dimethylamino pyridine, diisopropyl ethyl amines, N-methyl morpholines, with triethylamine being preferred. A sufficient amount of the base can be ascertained by one skilled in the art which permits the formation of the compounds of Formula I.

Preferably the base is added to the alcohol (5) and that mixture added dropwise to the acid halide or acid anhydride in an appropriate solvent. Examples of appropriate solvents are chloroform, methylene chloride, or toluene, all of which are readily available, with chloroform being preferred.

The temperature of the reaction may be at a range of about 0–25° C. The reaction mixture may be stirred for from a few hours to overnight to enhance the reaction. Catalysts may also be added for enhancement of reaction times, e.g., 4-dimethylaminopyridine or the like.

The starting materials for the acid halide (RCOX) are readily available for those skilled in the art. For example, Aldrich Chemical company provides stearoyl chloride, heptadecanoyl chloride, palmitoyl chloride, myristoyl chloride, isovaleryl chloride, valeryl chloride, hexanoyl chloride, hexanoyl chloride, heptanoyl chloride, octanoyl chloride, nonanoyl chloride, decanoyl chloride, undecanoyl chloride and lauroyl chloride. For those acid halides not readily available, one skilled in the art may prepare the acid halide desired. For example, a carboxylic acid may be mixed with a halide donor to produce the desired acid halide. One example of this is to mix carboxylic acid (0.17 mol), methylene chloride (660 mL) and dimethylformamide (0.5 mL) under a nitrogen atmosphere. Add oxalyl chloride (0.2 mol) over about 5 minutes with stirring. Stir at ambient temperature for 3 hours and evaporate the solvent in vacuo to the acid chloride. Another method is to dissolve the carboxylic acid (10 mmol) in methylene chloride (50 mL). Cool to 0° C., place under a nitrogen atmosphere and add, by dropwise addition, thionyl chloride (11 mmol). Stir at room temperature for several hours and evaporate the volatiles in vacuo to give the acid chloride. The carboxylic acids are readily available or can be easily made by those skilled in the art.

The starting materials for the acid anhydrides $(RCO)_2O$ are readily available for those skilled in the art. For example, Aldrich Chemical company provides butryic anhydride, isobutyric anhydride, valeric anhydride, 2-2,dimethylglutaric anhydride, and phthalic anhydride. Alternatively, acid anhydrides may be synthesized by methods well known in the art.

The starting materials for the acids ($RCO_2H$) are readily available or may be synthesized by methods well know in the art. For example, see *Advanced Organic Chemistry, Reactions, Mechanisms, and Structure, 4th ed.*, John Wiley & Sons, New York 1992, incorporated herein by reference. Aldrich Chemical Company also provides isovaleric acid, valeric acid, tert-butylacetic acid, 2,2dimethylbutyric acid, 2-ethylbutyric acid, hexanoic acid, 3-methylvaleric acid, 4-methylvaleric acid, heptanoic acid, octanoic acid, 2-propylpentanoic acid, nanoic acid, decanoic acid, undecanoic acid, lauric acid, tridecanoic acid, myristoleic acid, myristic acid, pentadecanoic acid, palmitic acid, heptadecanoic acid, stearic acid, nonadecanoic acid, eicosanoic acid.

The following examples are being present to further illustrate the invention. However, they should not be construed as limiting the invention in any manner.

EXAMPLE 1

Starting Material

Example 1, Steps A–D, demonstrates the preparation of the starting material (±)-alpha(2,3-dimethoxyphenyl)-1-[2-(4-fluorophenyl)ethyl]-4-piperidinemethanol, structure 1, Scheme I.

A) 1-[2-(4-Fluorophenyl)ethyl]-4-piperidinecarboxamide

A solution of isonipecotamide (10.9 g, 85.0 mmol), 2-(4-fluorophenyl)ethyl bromide (15.7 g, 77.3 mmol), and $K_2CO_3$ (2.3 g, 167 mmol) was prepared in DMF (280 mL) and stirred under argon at 90–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2× with water, dried ($MgSO_4$), filtered, and evaporated to a oily solid. The solid was recrystallized from EtOAc to afford 1-[2-(4-fluorophenyl)ethyl]-4-piperidinecarboxamide as a white powder, m.p. 177–178° C. (decomp.). Anal. Calcd for $C_{14}H_{19}FN_2O$: C, 67.18; H, 7.65; N, 11.19. Found: C, 67.25; H, 7.67; N, 11.13.

B) 4-Cyano-1-[2-(4-fluorophenyl)ethyl]piperidine

To stirred phosphorus oxychloride (25 mL, 41.12 g, 268 mmol) and sodium chloride (5.1 g, 87.3 mmol) was added 1-[2-(4-fluorophenyl)ethyl]-4-piperidinecarboxamide (8.9 g, 35.6 mmol) portionwise. After complete addition, the solution was refluxed for 2 hours. The cooled solution was carefully poured into dilute $NH_4OH$ to destroy the $POCl_3$. The aqueous solution was cooled to 0° C., then extracted 2× with $CH_2Cl_2$. The combined organic layers were dried ($MgSO_4$), filtered, and evaporated to afford 8.1 g of an oily solid. The solid was distilled, (b.p. 150° C., 0.1 mm Hg), to afford a clear, colorless oil that solidified. This material was crystallized from hexane to afford 4-cyano-1-[2-(4-fluorophenyl)ethyl]piperidine as white needles, m.p. 47–48° C. Anal. Calcd for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl)-ethyl]piperidine (1.00 g, 4.3 mmol) in THF (20 mL) under argon at 0° C. was added DIBAL-H (4.6 mL of a 1.0 M solution in THF, 4.6 mmol) via syringe. After stirring overnight at room temperature, 10% aqueous HCl (25 mL) was added and the solution was stirred for 3 hours. The entire mixture was then poured into 10% aqueous NaOH (50 mL), then extracted 2× with ether. The combined organic layers were washed with brine, dried ($MgSO_4$), filtered, and evaporated to afford a pale yellow oil. The oil was chromatographed on silica gel, eluting with EtOAc. The appropriate fractions were combined and evaporated to afford an oil. This oil was distilled (b.p. 166° C., 0.05 mm Hg) to afford 1-[2-(4-fluorophenyl)ethyl]-4-piperidinecarboxaldehyde, obtained as a colorless oil. Anal. Calcd for $C_{14}H_{18}FNO$: C, 71.46; H, 7.71; N, 5.95. Found: C, 71.08, H, 7.81; N, 5.86.

D) (±)-alpha(2,3-Dimethoxyphenyl)-1-[2-(4-fluorophenyl)ethyl]-4-piperidinemethanol To a stirred solution of veratrole (0.93 g, 6.7 mmol) in THF (20 mL) under argon at 0° C. was added n-BuLi (2.7 mL of a 2.5 M solution in hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an addition funnel. The cooling bath was removed and the solution was allowed to stir for 2 hours. Water was added, the layers separated, and the aqueous layer was extracted with EtOAc. The combined organic layers were washed with brine, dried ($MgSO_4$), filtered, and chromatographed on silica gel, eluting with acetone. The appropriate fractions were combined and evaporated to afford a white solid. The solid was recrystallized from hexane to afford racemic alpha(2,3-dimethoxyphenyl)-1-[2-(4-fluorophenyl)ethyl]-4-piperidinemethanol as shiny white needles, m.p. 126–127° C.

Anal. Calcd for $C_{22}H_{28}FNO_3$: C, 70.75; H, 7.56; N, 3.75. Found: C, 70.87; H, 7.65; N, 3.68.

EXAMPLE 2

Starting Material

Example 2, Steps A–F, demonstrate an alternative manner of preparing (±)-alpha(2,3-dimethoxyphenyl)-1-[2-(4-fluorophenyl)-ethyl]-4-piperidinemethanol, structure 1.

A) 1-(1,1-Dimethylethyl)-1,4-piperidinedicarboxylic acid

To isonipecotic acid (107.5 g, 832 mmol) stirred in 1N NaOH (40 g NaOH in 900 mL $H_2O$) and tert-butanol (1800 mL) was added di-tert-butyl dicarbonate (200 g, 916 mmol) in portions. After stirring overnight, the solution was concentrated and the resulting water layer was acidified with aqueous HCl. This acidic aqueous layer was extracted 3× with ether. The combined organic layers were washed with water, brine, dried ($MgSO_4$), filtered, and evaporated to a white solid, which was recrystallized from EtOAc/hexane (300 mL/200 mL) to afford 1-(1,1-dimethylethyl)-1,4-piperidinedicarboxylic acid as white needles, m.p. 147–149° C.

B) 4-(N-Methoxy-N-methylcarboxamido)-1-piperidinecarboxylic acid 1,1-dimethylethyl ester To a stirred solution of 1-(1,1-dimethylethyl)-1,4-piperidinedicarboxylic acid (50.0 g, 218 mmol) in anhydrous $CH_2Cl_2$ (500 mL) under $N_2$ in a 2 L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl, twice with saturated $NaHCO_3$, once with brine, dried ($MgSO_4$), filtered, and evaporated to an oil. Distillation afforded 4-(N-methoxy-N-methylcarboxamido)-1-piperidinecarboxylic acid 1,1-dimethylethyl ester as a clear oil, b.p. 120–140° C., 0.8 mm.

C) 4-(2,3-Dimethoxybenzoyl)-1-piperidinecarboxylic acid 1,1-dimethylethyl ester n-Butyl lithium (14.5 mL of a 2.5 M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous $NH_4Cl$ was added and the mixture was allowed to stir overnight. The layers were separated and the aqueous layer was extracted with ether. The combined organic layers were washed with brine, dried ($MgSO_4$), filtered, and evaporated to afford an amber oil. The oil was chromatographed on silica gel, eluting with 20% EtOAc in hexane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil.(b.p. 225–250° C., 0.05 mm). Anal. Calcd for $C_{19}H_{27}NO_5$: C, 65.31; H, 7.79; N, 4.01. Found: C, 65.04; H, 7.92; N, 4.11.

D) 4-(2,3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd for $C_{14}H_{19}NO_3.CF_3CO_2H$: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried ($MgSO_4$), filtered, and evaporated to afford 4-(2,3-dimethoxyphenyl)-4-piperidinylmethanone as an oil.

E) (2,3-Dimethoxyphenyl)[1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4-fluorophenyl)ethyl bromide (6.52 g, 32.1 mmol) was prepared in DMF (90 mL), treated with $K_2CO_3$ (7.0 g, 50.7 mmol), then stirred and heated at 80° C. under argon overnight. The cooled solution was poured into a partition of 2/1 EtOAc/toluene and water. The layers were separated and the aqueous layer was extracted with 2/1 EtOAc/toluene. The combined organic layers were washed 2× with water, 1× with brine, dried ($MgSO_4$), filtered, and evaporated to afford 11.0 g of an oil. The oil was chromatographed on silica gel, eluting with EtOAc. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225–227° C. (decomp). Anal Calcd for $C_{22}H_{26}FNO_3.HCl$: C, 64.78; H, 6.67; N, 3.43. Found: C, 64.44; H, 6.73; N, 3.41.

F) (±)-alpha-(2,3-Dimethoxyphenyl)-1-[2-(4-fluorophenyl) ethyl]-4-piperidinemethanol To a stirred solution of (2,3-dimethoxyphenyl)[1-[2-(4-fluorophenyl)ethyl]-4-piperidinyl]methanone (6.0 g, 16.2 mmol) in MeOH (100 mL) at 0° C. was added $NaBH_4$ (1240 mg, 32.8 mmol) in two portions, over a one hour period. After stirring overnight, the solution was concentrated to a solid. The solid was partitioned between water and ether. The layers were separated and the aqueous layer was extracted with ether. The combined organic layers were washed with brine, dried ($MgSO_4$), filtered, and evaporated to a solid. The solid was chromatographed on silica gel, eluting with acetone. The appropriate fractions were combined and evaporated to afford a white solid. The solid was recrystallized from cyclohexane to afford (±)-alpha-(2,3-dimethoxyphenyl)-1-[2-(4-fluorophenyl)-ethyl]-4-piperidinemethanol as white needles, m.p. 126–127° C.

Anal. Calcd for $C_{22}H_{28}FNO_3$: C, 70.75; H, 7.56; N, 3.75. Found: C, 70.86; H, 7.72; N, 3.93.

EXAMPLE 3

Starting Material

This example demonstrates the preparation of the alcohol, structure 5.

Preparation of (+)-alpha-(2,3-Dimethoxyphenyl)-1-[2-(4-fluorophenyl)ethyl]4-piperidinemethanol A) Preparation of Diastereomers.

A solution of 3.90 g (10.4 mmol) of (±)-alpha-(2,3-dimethoxyphenyl)-1-[2-(4-fluorophenyl)ethyl]-4-piperidinemethanol, 1.74 g (10.4 mmol) of S-(+)-alpha-methoxyphenylacetic acid, 2.15 g (10.4 mmol) of 1,3-dicyclohexylcarbodiimide and 0.1 g of 4-dimethylaminopyridine in chloroform (75 mL) was refluxed for 17 hours, allowed to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were rechromatographed to give additional material. Those fractions with Rf=0.2 were combined to give a single diastereomeric ester, (+,+)-(2,3-dimethoxyphenyl)[1-[2-(4-fluorophenyl)ethyl]-4-piperidinyl]methyl-alpha-methoxybenzeneacetate.

B) Preparation of (+)-alpha-(2,3-Dimethoxyphenyl)-1-[2-(4-fluorophenyl)ethyl]-4-piperidinemethanol To a stirred solution of 0.97 g (1.9 mmol) of the above mentioned diastereomeric ester, Rf=0.2, in 25 mL of methanol was added 0.5 g (3.6 mmol) of potassium carbonate and 5.0 mL of water. After stirring 17 hours at room temperature the reaction mixture was diluted with water and extracted twice with methylene chloride. The combined extracts were washed with water, brine and dried over $MgSO_4$. After filtering, the filtrate was concentrated to an oil and crystallized from 40 mL of cyclohexane/hexane (1:1) to give (+)-alpha-(2,3-dimethoxyphenyl)-1-[2-(4-fluorophenyl) ethyl]-4-piperidinemethanol, m.p. 112–113° C., $[\alpha]_D^{20}$=+13.9°.

EXAMPLE 4

The compound of the present invention can be shown to be effective by clinical trials in humans and certain behavioral tests in animals.

Examples of methods in human clinical trials follow.

1. Bristol Activities of Daily Living Scale, Bucks, Ashworth, Wilcock Siegfried 1996 (incorporated herein by reference). The patient is observed and rated according to their ability to perform certain functions such as the ability to prepare food, eat, drink, dress, shop, communicate, etc., i.e., the ability to perform normal daily functions and to be appropriately oriented to time and space.
2. Senile Dementia Associated Sleep Disorder (SDASD), Cacabelos, Laredo, Couceiro, Alvarez 1999 (incorporated herein by reference). Conditions are noted for sleep disturbances such as initial insomnia, nocturnal sleep disruption, delayed insomnia, fragmented sleep patterns, etc.
3. Cornell Scale for Depression in Dementia., Alexopoulos, Abrams, Young, Shamoian 1988 (incorporated herein by reference). Mood related signs, behavioral disturbances, physical signs, cyclic functions and ideational disturbances are noted and rated.
4. Cognitive Assessment Systems, e.g., Learning and Motivation 4: 327–342; International Journal of Geriatric Psychiatry 10: 189–201 (incorporated herein by reference). Patient is rated on their ability to recognize words, pictures, etc.
5. Unified Parkinson's Disease Rating Scale (UPDRS), Langston, Widner, Goetz, Brooks, Fahn, Freeman, Watts 1992). The patient is observed for typical motor and gait symptoms present in Parkinsons.
6. Hallucinations/Delusions. The patient is interviewed and observed regarding hallucinations and delusions and rated according to set protocol.
7. Polysomnography to study increase in slow wave sleep.

EXAMPLE 5

Administration of scopolamine, an antagonist at the acetylcholine muscarinic receptor, has been associated with hallucinations and behavioral disturbances in humans (*Brain and Cognition* (1995) 28:240–258). Also, scopolamine-induced hyperlocomotion in the rat has been used as a model of behavioral disturbances related to cholinergic deficiency states (*Jpn J Pharmacol* (1999) 79 (Suppl. 1):43P). Cholinergic deficiency states include various neurodegenerative diseases such as Alzheimer's disease, Dementia with Lewy Bodies, Charles Bonnet Syndrome, delirium and Parkinson's disease.

Experimental Procedure. All procedures were conducted in normal white light conditions. Rats (1 per box) were first acclimated to test boxes (45×22×20 cm; clear polycarbonate with a plastic top) for 90 minutes. Each rat was then given two intraperitoneal injections (vehicle+vehicle, vehicle+scopolamine, test compound dose 1+scopolamine, test compound dose 2+scopolamine, test compound dose 3+scopolamine or test compound dose 4+scopolamine) and replaced into its test box, which was placed into an activity counter (Opto-Varimex Mini, Columbus Instruments, Columbus, Ohio). Testing commenced immediately. Locomotor activity was recorded for 60 min in the activity counter, which was equipped with 15 photoelectric light sources spaced at 2 cm intervals and 1 cm above the floor. Each interruption of a photoelectric light beam was recorded as a single activity count by a microprocessor-based control system. Testing took place between 10:00 a.m. and 5:00 p.m., with all groups counterbalanced for time of testing. The experimenter was blind to treatment group during the experiment.

Results. M100907 (0.03–1 mg/kg) and risperidone (0.03–1 mg/kg) significantly antagonized scopolamine-stimulated locomotion (see FIGS. 1–2 and Tables 1–2; Abbreviations: VEH=vehicle, SCOP=scopolamine). M100907 restored activity to baseline (vehicle) level, but risperidone at the two higher doses reduced activity below baseline level.

Conclusions. The present results demonstrate that the selective 5-HT2A antagonist M100907 antagonized scopolamine-stimulated locomotion in rats without reducing activity levels below baseline. The $5\text{-HT}_{2A}/D_2$ antagonist risperidone also antagonized scopolamine-stimulated locomotion, but the two higher doses reduced activity levels below baseline. This could be due to risperidone's potent $D_2$ antagonist activity, which may have resulted in sedation or motor dysfunction.

TABLE 1

M100907: Group means of 60 min activity count totals +/− SEM

| Treatment | n | MEAN | +/− SEM |
|---|---|---|---|
| VEH + VEH | 6 | 1687 | 457 |
| VEH + SCOP 0.75 | 6 | 5753 | 1386 # |
| M100907 0.03 + SCOP 0.75 | 6 | 3181 | 804 * |
| M100907 0.1 + SCOP 0.75 | 6 | 2378 | 306 * |
| M100907 0.3 + SCOP 0.75 | 6 | 2087 | 752 * |
| M100907 1 + SCOP 0.75 | 6 | 2231 | 737 * |

TABLE 2

Risperidone: Group means of 60 min activity count totals +/− SEM

| Treatment | n | MEAN | +/− SEM |
|---|---|---|---|
| VEH + VEH | 8 | 2484 | 441 |
| VEH + SCOP 0.75 | 8 | 7975 | 1880 ## |
| RISPERIDONE 0.03 + SCOP 0.75 | 8 | 4615 | 1382 * |
| RISPERIDONE 0.1 + SCOP 0.75 | 8 | 4037 | 1156 * |
| RISPERIDONE 0.3 + SCOP 0.75 | 8 | 1795 | 336 ** |
| RISPERIDONE 1 + SCOP 0.75 | 8 | 772 | 203 *** |

Newman-Keuls Test
$p < 0.05$, ## $p < 0.01$ vs. VEH + VEH
* $p < 0.05$,  $p < 0.01$, * $p < 0.001$ vs. VEH + SCOP

EXAMPLE 6

M100907 (0.1 and 1 mg/kg) significantly enhanced social memory in mice. Male CD-1 mice (30–35 grams) were first acclimated to the test room for approximately 1 hour. The mice were then administered vehicle or M100907 (0.01, 0.1 or 1 mg/kg p.o.) 2 hours prior to their baseline test. For the baseline test, unfamiliar pairs of mice were placed into a test chamber (plexiglas mouse cage with sawdust bedding). The duration of social interaction of the two mice (sniffing, anogenital exploration, nosing, grooming, licking, pawing, playing copulatory attempts) was observed and recorded for a period of five minutes and was registered cumulatively as total seconds of contact. Twenty-four hours later, the animals were given a retest without any drug treatment. At the retest, the now familiar partners from the baseline test were placed into the test chamber for a second confrontation and the duration of social interaction was again measured. Social memory was defined as a significant decrease in duration of social contact from baseline to retest. Testing took place in normal white light conditions between the hours of 8:30 am and 3:00 pm. The experimenter was blind to the treatment group until the completion of the experiment. The results represent combined data (n=36 per group total) from two studies. Data were analyzed using the Mann-Whitney test.

TABLE 3

| Treatment | n | MEAN | +/− SEM |
| --- | --- | --- | --- |
| VEH (baseline) | 36 | 25.82 | 2.03 |
| VEH (retest) | 36 | 23.88 | 1.82 |
| M100907 0.01 (baseline) | 36 | 23.05 | 1.28 |
| M100907 0.01 (retest) | 36 | 20.3 | 1.41 |
| M100907 0.1 (baseline) | 36 | 25.5 | 2.0 |
| M100907 0.1 (retest) | 36 | 21.21 | 1.57 * |
| M100907 1 (baseline) | 36 | 25.0 | 1.89 |
| M100907 1 (retest) | 36 | 18.1 | 1.47 * |

* $p < 0.05$ vs. baseline test using Mann-Whitney test

The dosage range at which the compounds of Formula I exhibit their ability treat patients with DLB depends upon the severity of the disease, the patient, the formulation, other underlying disease states that the patient is suffering from, and other medications that may be concurrently administered to the patient. Generally, the compounds of Formula I will exhibit their therapeutic activities between about 0.001 mg/kg of patient body weight/day to about 100 mg/kg of patient body weight/day. The dosage of the compounds of the present invention may be determined by administering the compound to an animal and determining the plasma level of the active ingredient by known procedures.

The compound of the present invention can be formulated into pharmaceutical dosage forms using techniques well known in the art. For oral administration, the compound can be formulated into solid or liquid preparation such as capsules, pills, tablets, lozenges, melts, powders, suspensions or emulsions. For parenteral administration, the compound or its salts may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetable, or synthetic origin. The pharmaceutical carrier may also contain preservatives, buffers, etc. as are known in the art.

All cites to publications and patents herein are hereby incorporated by reference.

What is claimed is:

1. A method of treating a patient suffering from behavioral or psychological symptoms associated with a disease selected from the group consisting of Alzheimer's disease, Lewy body dementia, and Parkinson's disease comprising administering to said patient a therapeutically effective amount of (+)-(α-2,3-dimethoxyphenyl)-1-[2-(4-fluorophenyl)ethyl]-4-piperidinemethanol, or a pharmaceutically acceptable salt thereof; or a prodrog, its stereoisomer or pharmaceutically acceptable salt thereof, wherein the prodrug is

FORMULA II

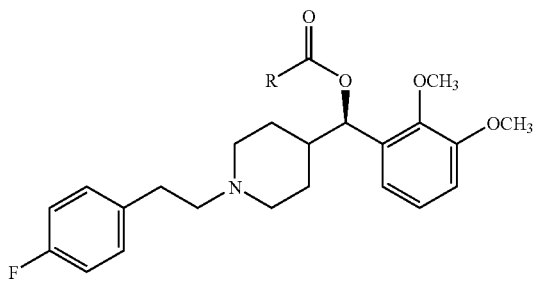

wherein R is C1–C20 alkyl.

2. The method of claim 1 wherein the disebse is Lewy body dementia.

3. The method of claim 1 wherein the disease is Alzheimer's disease.

4. The method of claim 1 wherein the disease is Parkinson's disease.

5. The method of claim 1 wherein R is C5–C20.

6. The method of claim 1 wherein R is C9.

7. The method of claim 1 wherein a therapeutically effective amount of (+)-α-(2,3-dimethoxyphenyl)-1-[2-(4-fluorophenyl)ethyl]-4-piperidinemethanol or a pharmaceutically acceptable salt thereof is administered to the patient.

8. The method of claim 1 wherein a therapeutically effective amount of the prodrug, its stereoisomer or a pharmaceutically acceptable salt thereof is administered to the patent.

* * * * *